(12) United States Patent
Belley

(10) Patent No.: US 8,815,535 B2
(45) Date of Patent: Aug. 26, 2014

(54) DISK DIFFUSION ASSAY FOR ORITAVANCIN

(75) Inventor: Adam Belley, Beaconsfield (CA)

(73) Assignee: The Medicines Company, Parsippany, NJ (US)

( * ) Notice: Subject to any disclaimer, the term of this patent is extended or adjusted under 35 U.S.C. 154(b) by 0 days.

(21) Appl. No.: 13/559,060

(22) Filed: Jul. 26, 2012

(65) Prior Publication Data

US 2013/0029371 A1   Jan. 31, 2013

Related U.S. Application Data

(60) Provisional application No. 61/511,608, filed on Jul. 26, 2011, provisional application No. 61/642,099, filed on May 3, 2012.

(51) Int. Cl.
*C12Q 1/18* (2006.01)

(52) U.S. Cl.
USPC .... 435/32; 435/283.1; 435/288.7; 435/288.3; 514/2.4; 514/3.1

(58) Field of Classification Search
USPC ........... 435/32, 33, 34, 288.3, 288.7; 514/2.4, 514/3.1
See application file for complete search history.

(56) References Cited

U.S. PATENT DOCUMENTS

| 4,448,534 A | 5/1984 | Wertz et al. |
| 6,103,228 A | 8/2000 | Heins et al. |
| 6,153,400 A | 11/2000 | Matsumura et al. |

OTHER PUBLICATIONS

Anderson, "New Surface Active Antibiotics" (1946) Seventh Annual Meeting of the Society for Investigative Dermatology: 25-33.*
"Disk Diffusion Susceptibility" (2003) NCCLS: vol. 16.*
Hotchkiss, "The Nature of the Bacterialcidal Action of Surface Active Agents" (1946) Annals of the New York Academy of Sciences vol. 46: 479-493.*
Wanger, A. (2007). Disk diffusion test and gradient mehtodologies. In R. Schwalbe., L. Steele-Moore., & A.C. Goodwin (Eds.), Antimicrobial Susceptibility Testing Protocals (pp. 53-73). New York, NY: CRC Press, Taylor & Francis Group, LLC. DOI: 10.1201/97814495. ch3.*
Arhin, F. et al., Effect of Polysorbate 80 on Oritavancin Binding to Plastic Surfaces: Implications for Susceptibility Testing, Antimicrob. Agents Chemother., 2008:52(5):1597-1603.
International Search Report for corresponding PCT/US2012/048329 dated Feb. 13, 2013.

* cited by examiner

*Primary Examiner* — Jon P Weber
*Assistant Examiner* — Teresa E Knight
(74) *Attorney, Agent, or Firm* — Roylance, Abrams, Berdo & Goodman LLP

(57) ABSTRACT

The present invention is directed to a disk diffusion assay for determining susceptibility of bacteria to a glycopeptide antibiotic. The assay includes improvements over conventional assays due to the inclusion of polysorbate 80 and Span 80 in the antibacterial solution used to impregnate paper disks used in the assay.

20 Claims, 2 Drawing Sheets

DISK DIFFUSION ASSAY FOR ORITAVANCIN

CROSS-REFERENCE TO RELATED APPLICATIONS

The present application claims benefit of U.S. provisional application No. 61/511,608, filed Jul. 26, 2011, and U.S. provisional application No. 61/642,099, filed May 3, 2012, the contents of both of which are incorporated herein by reference in their entireties.

BACKGROUND OF THE INVENTION

Antimicrobial susceptibility testing (ASTs) devices provide critical information that aids in selection of effective and appropriate antimicrobial therapy. Several AST devices are available from device manufacturers and they include disk diffusion assays, E-test strips (AB bioMerieux), and automated systems such as VITEK™ (bioMerieux), Phoenix (Becton Dickinson) and Microscan WALKAWAY™ (Siemens). Because of its simplicity, the disk diffusion assay is a widely used AST device.

The investigational lipoglycopeptide oritavancin exhibits an inherent capacity to bind to plastic and glass surfaces which has consequently confounded measurement of its true potency in susceptibility tests (Arhin, F F, et al. 2008. *Antimicrob Agents Chemother* 52:1597-603). To date, only the broth microdilution (BMD) minimal inhibitory concentration (MIC) test is a reference method accepted by the Clinical Laboratory Standards Institute (CLSI) for use in determining the susceptibility of a bacterial isolate to oritavancin (Methods for Dilution Antimicrobial Susceptibility Tests for Bacteria That Grow Aerobically; Approved Standard, CLSI document M7-A8, 8th ed. Clinical and Laboratory Standards Institute, Wayne, Pa. 2009; Performance Standards for Antimicrobial Susceptibility Testing; Eighteenth Informational Supplement, CLSI document M100-S18, 7th ed. Clinical and Laboratory Standards Institute, Wayne, Pa. 2008). Recent developments have demonstrated that inclusion of 0.002% polysorbate-80 (P80) during BMD MIC testing minimizes loss of oritavancin due to non-specific binding and allows for accurate determination of the MIC of a clinical isolate (Arhin, F F, et al. 2008. *Antimicrob Agents Chemother* 52:1597-603).

Because BMD MIC testing is technically cumbersome, other methods that simplify susceptibility testing for oritavancin would be advantageous to clinical microbiologists. Previous studies that evaluated the feasibility of an agar-based disk diffusion assay for oritavancin concluded that slow diffusion of oritavancin in agar results in zones of clearance (zone diameters) that do not meet the minimum requirements recommended by the CLSI (≥15 mm) under standard testing conditions (Sahm, D F, et al. 2003. Feasibility study to assess disk diffusion as a method for testing the susceptibility of bacterial pathogens to oritavancin. Unpublished internal report; Turnbull, B. 2007. Disk diffusion feasibility study for oritavancin susceptibility testing. Unpublished internal report).

Development of a disk diffusion assay that permits accurate determination of the susceptibility of a bacterial isolate to oritavancin, under the minimum requirements recommended by the CLSI, would greatly aid in rapid and accurate selection of therapy using oritavancin.

BRIEF SUMMARY OF THE INVENTION

The present invention is directed to disk diffusion assays for determining susceptibility of bacteria to a glycopeptide antibiotic.

In a first embodiment, the present invention is directed to a disk diffusion assay for determining susceptibility of bacteria to a glycopeptide antibiotic that comprises: a) impregnating a paper disk with a solution comprising a glycopeptide antibiotic and polysorbate 80, b) placing the impregnated disk on the surface of a bacteria-coated media plate, c) incubating the plate of b) under conditions promoting bacterial growth, and d) measuring a zone of inhibition around the disk.

In certain aspects of this embodiment, polysorbate 80 present is present in the solution at a concentration of between about 0.002% and about 10% v/v, or at a concentration of between about 1% and about 8% v/v. In other aspects, polysorbate 80 present is present in the solution at a concentration of about 2.5% or about 5% v/v.

In certain aspects of this embodiment, the glycopeptide antibiotic is present in the solution at a concentration of between about 0.5 and about 50 mg/ml, or at a concentration of between about 1 and about 20 mg/ml. In related aspects, the paper disk is impregnated with about 180 ug of the glycopeptide antibiotic, or with about 360 ug of the glycopeptide antibiotic.

In certain aspects of this embodiment, the impregnated disk is maintained at room temperature for at least about 12 hours, for at least about 4 days, for at least about 8 days, or for at least about 30 days, before it is placed on the media plate.

In certain aspects of this embodiment, the plate of b) on which the disk has been placed is maintained at room temperature for at least about 1 hour, at least about 3 hours or at least about 6 hours, before the incubating step c). Alternatively, the plate of b) is maintained at temperature of about 4° C. for at least about 1 hour, at least about 3 hours or at least about 6 hours, before the incubating step c). In certain assays, the incubating step c) is conducted at about 37° C. As an example, in one aspect the plate of b) is maintained at room temperature for at least about 3 hours before the incubating step c), and the incubating step c) is conducted at about 37° C., or the plate of b) is maintained at about 4° C. for at least about 3 hours before the incubating step c), and the incubating step c) is conducted at about 37° C.

In certain aspects of this embodiment, the glycopeptide antibiotic is oritavancin.

In certain aspects of this embodiment, the zone of inhibition measured in d) is at least about 15 mm in diameter.

In a second embodiment, the present invention is directed to a disk diffusion assay for determining susceptibility of bacteria to a glycopeptide antibiotic that comprises: a) impregnating a paper disk with a solution comprising a glycopeptide antibiotic and polysorbate 80, wherein polysorbate 80 is present in the solution at a concentration of between about 0.002% and about 10% v/v, b) maintaining the impregnated disk at room temperature for at least about 8 days, c) placing the impregnated disk on the surface of a bacteria-coated media plate, and maintaining the plate at 4° C. for at least about 1 hour, d) incubating the plate of c) under conditions promoting bacterial growth, and e) measuring a zone of inhibition around the disk.

In certain aspects of this embodiment, polysorbate 80 is present in the solution at a concentration of between about 1% and about 8% v/v. In other aspects, polysorbate 80 is present in the solution at a concentration of about 2.5% or about 5% v/v.

In certain aspects of this embodiment, the glycopeptide antibiotic is present in the solution at a concentration of between about 0.5 and about 50 mg/ml, or at a concentration of between about 1 and about 20 mg/ml. In related aspects, the paper disk is impregnated with about 180 ug of the glycopeptide antibiotic, or about 360 ug of the glycopeptide antibiotic.

In certain aspects of this embodiment, the impregnated disk is maintained at room temperature for at least about 4 days, at least about 8 days or for at least about 30 days.

In certain aspects of this embodiment, the plate on which the disk has been placed is maintained at about 4° C. for at least about 3 hour, or the plate is maintained at 4° C. for at least about 6 hours. In other aspects, the plate of c) is maintained at room temperature for at least about 3 hours before the incubating step d), and the incubating step d) is conducted at about 37° C., or the plate of c) is maintained at about 4° C. for at least about 3 hours before the incubating step d), and the incubating step d) is conducted at about 37° C. As an example, in one aspect the plate of c) is maintained at room temperature for at least about 3 hours before the incubating step d), and the incubating step d) is conducted at about 37° C., or the plate of c) is maintained at about 4° C. for at least about 3 hours before the incubating step d), and the incubating step d) is conducted at about 37° C.

In certain aspects of this embodiment, the glycopeptide antibiotic is oritavancin.

In certain aspects of this embodiment, the zone of inhibition measured in e) is at least about 15 mm in diameter.

In a third embodiment, the present invention is directed to a disk diffusion assay for determining susceptibility of bacteria to oritavancin that comprises: a) impregnating a paper disk with a solution comprising oritavancin and polysorbate 80, wherein polysorbate 80 is present in the solution at a concentration of about 5% v/v, b) maintaining the impregnated disk at room temperature for at least about 8 days, c) placing the impregnated disk on the surface of a bacteria-coated media plate, and maintaining the plate at 4° C. for at least about 3 hours, d) incubating the plate of c) under conditions promoting bacterial growth, and e) measuring a zone of inhibition around the disk.

In certain aspects of this embodiment, oritavancin is present in the solution at a concentration of between about 0.5 and about 50 mg/ml, or at a concentration of between about 1 and about 20 mg/ml. In related aspects, the paper disk is impregnated with about 180 ug of oritavancin, or about 360 ug of oritavancin.

In certain aspects of this embodiment, the impregnated disk is maintained at room temperature for at least about 30 days.

In certain aspects of this embodiment, the plate is maintained in step c) at about 4° C. for at least about 6 hours, or the incubating step d) is conducted at about 37° C., or both.

In certain aspects of this embodiment, the zone of inhibition measured in e) is at least about 15 mm in diameter.

In a fourth embodiment, the present invention is directed to a disk diffusion assay for determining susceptibility of bacteria to a glycopeptide antibiotic that comprises: a) impregnating a paper disk with a solution comprising a glycopeptide antibiotic, polysorbate 80 and Span 80, b) placing the impregnated disk on the surface of a bacteria-coated media plate, c) incubating the plate of b) under conditions promoting bacterial growth, and d) measuring a zone of inhibition around the disk.

In certain aspects of this embodiment, the glycopeptide antibiotic is present in the solution at a concentration of between about 0.5 and about 5 mg/ml. In a specific aspect, the glycopeptide antibiotic is present in the solution at a concentration of about 1.25 mg/ml. In related aspects, the paper disk is impregnated with about 25 ug of the glycopeptide antibiotic.

In certain aspects of this embodiment, polysorbate 80 and Span 80 are present in the solution at a ratio of between about 75:25 and 25:75 v/v, between about 60:40 and 40:60 v/v, or between about 55:45 and 45:55 v/v, or polysorbate 80 and Span 80 are present in the solution at a ratio of 50:50 v/v. In related aspects, the combined concentration of polysorbate 80 and Span 80 present in the solution is between about 2.5% and about 5.5% v/v, or the combined concentration of polysorbate 80 and Span 80 present in the solution is about 4%. In a specific aspect, polysorbate 80 and Span 80 are present in the solution at a ratio of between about 55:45 and about 45:55 v/v, and at a concentration of between about 3% and about 5% v/v. In a further specific aspect, polysorbate 80 and Span 80 are present in the solution at a ratio of about 50:50 v/v and at a concentration of about 4% v/v.

In certain aspects of this embodiment, the impregnated disk is dried at room temperature before placement on the media plate. The impregnated disk is placed on the media plate within a few hours of drying, such as within about 1, 2, 3, 4, 5 or 6 hours of drying.

In certain aspects of this embodiment, the incubating step c) is conducted at about 37° C.

In certain aspects of this embodiment, the glycopeptide antibiotic is oritavancin.

In certain aspects of this embodiment, the zone of inhibition measured in d) is at least about 15 mm in diameter.

In a fifth embodiment, the present invention is directed to a disk diffusion assay for determining susceptibility of bacteria to a glycopeptide antibiotic that comprises: a) impregnating a paper disk with a solution comprising a glycopeptide antibiotic, polysorbate 80 and Span 80, wherein the glycopeptide antibiotic is present at a concentration of about 1.25 mg/ml, and wherein the polysorbate 80 and Span 80 are present in the solution at a concentration of about 4% v/v and in a ratio of about 50:50 v/v, b) placing the impregnated disk on the surface of a bacteria-coated media plate, c) incubating the plate of b) under conditions promoting bacterial growth, and d) measuring a zone of inhibition around the disk.

In certain aspects of this embodiment, the paper disk is impregnated with about 25 ug of the glycopeptide antibiotic.

In certain aspects of this embodiment, the impregnated disk is dried at room temperature before placement on the media plate.

In certain aspects of this embodiment, the incubating step c) is conducted at about 37° C.

In certain aspects of this embodiment, the glycopeptide antibiotic is oritavancin.

In certain aspects of this embodiment, the zone of inhibition measured in d) is at least about 15 mm in diameter.

DETAILED DESCRIPTION OF THE INVENTION

Figure 1:
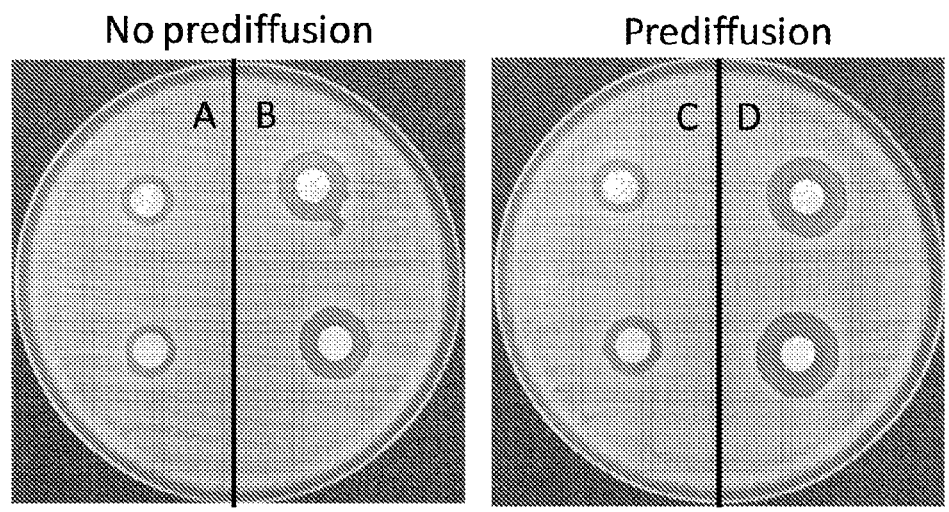
FIG. 1 shows the effect of prediffusion and 5% P80 on oritavancin zone diameters. Duplicate disks containing 360 μg of oritavancin, dissolved in either 0.002% P80 (A and C) or 5% P80 (B and D), were placed on each half of plates seeded with methicillin-susceptible S. aureus (MSSA) ATCC 25923. Zone diameters increased when 5% P80 instead of 0.002% P80 was used as excipient (compare A to B, or C to D) or when prediffusion was performed (compare A to C, or B to D). The drug-impregnated disks used in this study were stored at room temperature for 9 days prior to use.

The present invention is directed to agar-based antimicrobial disk diffusion assays that permit accurate determination of the susceptibility of bacteria to glycopeptide antibiotics, such as oritavancin. The assays can be conducted under the minimum requirements recommended by the CLSI.

The assays of the present invention incorporate one or more of several alterations to the traditional assay, resulting in disk diffusion assays that permit bacterial susceptibility determinations to be made for glycopeptide antibiotics. The alterations include one or more of: (i) use of polysorbate 80 (P80) or a mixture of P80 and Span 80 as a drug excipient, (ii) maintenance of antibiotic-impregnated disks at room temperature or at about 4° C. prior to use, and (iii) permitting prediffusion of antibiotic from the disk prior to incubation of the plates under conditions promoting bacterial growth. Different combinations of these alterations to the traditional assay conditions resulted in the production of zone diameters of >15 mm for many S. aureus strains, and up to 24 mm for the MSSA quality control strain ATCC 25923, when the glycopeptide antibiotic oritavancin was tested. The use of these conditions further resulted in a correlation between zone diameter and BMD MIC that was readily apparent with tested clinical isolates that span a broad range of oritavancin susceptibility (0.03 to 1 μg/ml). Thus, these alterations produce zone diameters that meet the minimum diameter requirement recommended by CLSI for an appropriate disk diffusion assay using glycopeptide antibiotics, such as oritavancin.

In general terms, the disk diffusion assays of the present invention comprise: a) impregnating a paper disk with a solution comprising an antibiotic and an excipient, wherein the excipient is P80 or P80 and Span 80, b) placing the impregnated disk on the surface of a bacteria-coated agar plate, c) incubating the plate under conditions promoting bacterial growth, and d) measuring a zone of inhibition around the disk.

As indicated above, the solution comprising the antibiotic will contain either P80 alone as an excipient, or both P80 and Span 80 as excipients, where the excipient(s) is diluted in water. The P80 and Span 80 used in the assays of the present invention can be readily obtained from a variety of sources. When the solution comprises P80 alone, the concentration of P80 may be between about 0.001% and about 15% v/v, and in some embodiments between about 0.002% and about 10% v/v, or between about 1% and about 8% v/v. In particular embodiments, the concentration of P80 in the solution is about 0.002% v/v, about 0.005% v/v, about 0.01% v/v, about 0.05% v/v, about 0.1% v/v, about 0.5% v/v, about 1% v/v, about 2% v/v, about 2.5% v/v, about 3% v/v, about 4% v/v, about 5% v/v, about 6% v/v, about 7% v/v, about 8% v/v, about 9% v/v, or about 10% v/v.

The skilled artisan will understand that surfactants related to P80, either through shared chemical structure or activity, may be used in place of P80 in each of the embodiments and aspects of the present invention. Such surfactants include polysorbate 20, polysorbate 40 and polysorbate 60; polyethylene glycol (PEG) of various molecular weight distributions, including but not limited to PEG 3350; block copolymers such a Pluronic®, including but not limited to Pluronic® F-68; nonionic detergents such as Triton X-100; and cyclodextrins, including but not limited to, hydroxypropyl-p-cyclodextrin (HPCD).

When the solution comprises both P80 and Span 80, the ratio of P80 to Span 80 may range from about 75:25 and about 25:75 v/v. In other embodiments, the combination will range from about 65:35 to about 35:65 v/v, from about 60:40 to about 40:60 v/v, from about 55:45 to about 45:55 v/v, or be about 50:50 v/v. The combined amount of the excipients in solutions comprising both P80 and Span 80 will range from about 0.002% to about 10% v/v, from about 2.5% and about 8% v/v, from about 3% and about 5% v/v, or be about 0.5%, 1%, 1.5%, 2%, 2.5%, 3%, 3.5%, 4%, 4.5%, 5%, 5.5%, or 6% v/v. In a particular embodiment, the solution is a 4% v/v solution of a 50:50 v/v combination of P80 and Span 80 in water. The antibiotic tested in the assays may be any glycopeptide antibiotic such as oritavancin (also termed N-(4-(4-chlorophenyl)benzyl)A82846B and LY333328), which is described in U.S. Pat. No. 5,840,684, incorporated herein by reference in its entirety. Other suitable glycopeptide antibiotics include, but are not limited to, dalbavancin vancomycin, teicoplanin, telavancin, bleomycin, ramoplanin, and decaplanin. The concentration of the antibiotic in the solution will vary based on such factors as the particular antibiotic being tested, the bacterial strains against which it is being tested, the size of the paper disk, and the amount of solution used to impregnate the disk. Generally, however, the antibiotic will present in the solution at a concentration of between about 0.5 and about 50 mg/ml, and in some embodiments between about 0.5 and about 5 mg/ml, between about 1 and about 30 mg/ml, or between about 5 and about 20 mg/ml. In particular embodiments, the antibiotic will present in the solution at a concentration of about 0.5 mg/ml, about 1 mg/ml, about 1.5 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml, about 7 mg/ml, about 7.5 mg/ml, about 8 mg/ml, about 8.5 mg/ml, about 9 mg/ml, about 9.5 mg/ml, about 10 mg/ml, about 10.5 mg/ml, about 11 mg/ml, about 11.5 mg/ml, about 12 mg/ml, about 12.5 mg/ml, about 13 mg/ml, about 13.5 mg/ml, about 14 mg/ml, about 14.5 mg/ml, about 15 mg/ml, about 15.5 mg/ml, about 16 mg/ml, about 16.5 mg/ml, about 17 mg/ml, about 17.5 mg/ml, about 18 mg/ml, about 18.5 mg/ml, about 19 mg/ml, about 19.50 mg/ml, or about 20 mg/ml.

The solution containing P80 and/or Span 80 and the antibiotic can be prepared by any suitable means. Typically, a solution of the desired concentration of P80 and/or Span 80 is produced, and then the antibiotic is dissolved in the excipient-containing solution to produce an antibiotic-containing excipient solution. The excipient-containing solution may be sterilized, such as through filter sterilization, prior to the addition of the antibiotic.

The paper disks used in the assays of the present invention can be any paper or cellulosic disk typically used in disk diffusion assays. For example, 6 mm, 9 mm or 13 mm diameter Whatman paper disks (Whatman Ltd.) or commercially available blank disks from Oxoid are commonly used, although other sizes may be used as well. Preferably, the paper disks are sterilized, such as through the use of ethanol, prior to being impregnated with the antibiotic-containing excipient solution. The amount of solution used to impregnate the disk will vary depending on such factors as the size of the disk, the antibiotic being tested, and the desired concentration of the antibiotic to be diffused from the disk. In general, when 6 mm diameter paper disks are used, between about 5 and 100 µl of solution are added to the disk. In particular embodiments, about 5 µl, about 10 µl, about 15 µl, about 20 µl, about 25 µl, about 30 µl, about 35 µl, about 40 µl, about 45 µl, or about 50 µl of solution are added to the disk.

The disks will be impregnated with an amount of antibiotic that will vary based on such factors as the particular antibiotic being tested, the bacterial strains against which it is being tested, the size of the paper disk, and the amount of solution used to impregnate the disk. Generally, however, the disks will be impregnated with between about 10 and about 1000 ug of the antibiotic, and in some embodiments between about 50 and about 500 ug of the antibiotic, or between about 100 and about 400 ug of the antibiotic. In particular embodiments, the disks will be impregnated with about 50 ug, 60 ug, 70 ug, 80 ug, 90 ug, 100 ug, 110 ug, 120 ug, 130 ug, 140 ug, 150 ug, 160 ug, 170 ug, 180 ug, 190 ug, 200 ug, 210 ug, 220 ug, 230 ug, 240 ug, 250 ug, 260 ug, 270 ug, 280 ug, 290 ug, 300 ug, 310 ug, 320 ug, 330 ug, 340 ug, 350 ug, 360 ug, 370 ug, 380 ug, 390 ug, or 400 ug of the antibiotic, or more.

After being impregnated with the antibiotic-containing excipient solution, the disks are permitted to dry at room temperature. In some embodiments of the invention, the disks are maintained at room temperature for a period of hours or days before use after they are dried. In other embodiments, the disks are used as soon as they are dry or within a few hours of drying, such as within about 1, 2, 3, 4, 5 or 6 hours of drying. In those embodiments where the disks are maintained at room temperature for a period of hours before use, they may be maintained for about 4, 6, 8, 10, 12, 14, 16, 18, 20, 22, 24 or more hours after they are impregnated with the antibiotic-containing excipient solution. In those embodiments where the disks are maintained at room temperature for a period of days before use, they may be maintained for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days after they are impregnated with the antibiotic-containing excipient solution. When the disks are maintained at room temperature for a period of hours or days before use, they may be maintained in the presence of ambient light or in the dark. In a preferred embodiment, the disks are used within a few hours after they are dried at room temperature. In another preferred embodiment, the disks are maintained at room temperature for about 8 days after drying and prior to use.

The disk diffusion assays of the present invention are conducted on media plates, where the media is agar, agarose or other gelling agent, preferably in the context of a cell culture plate. The particular size and shape of the culture plate has little bearing on the assay, however, polystyrene plates measuring 60 mm×15 mm are suitable, as are polystyrene plates measuring 100 mm×20 mm, or 150 mm×25 mm The identity of the gelling agent will depend on the bacterial strain being tested, and the skilled artisan will be readily able to determine which gelling agent to use for a particular bacterial strain. As an example, cation-adjusted Mueller Hinton agar can be used when the bacterial strain to be tested is *Staphylococcus aureus*. The plates and gelling agent are thus those typically used when conducting a standard disk diffusion assay.

The bacterial strain being tested is typically grown in a liquid media culture to a desired concentration, or as colonies on agar medium and then suspended in liquid, that is measured via optical density and which will depend on the particular bacterial strain being tested. As an example, an optical density of about 0.1 at 600 nm or 0.5 McFarland standard is desirable when the bacterial strain to be tested is *S. aureus*. An aliquot of the bacterial suspension is then seeded onto an agar plate. A swab or spreader may be used to uniformly coat the surface of the agar with the suspension. Calcium alginate swabs are particularly good at creating a uniform bed of bacteria without scoring the media. The plate may then be maintained at room temperature for a period of time before the impregnated disks are placed onto the surface of the agar, or the impregnated disks may be placed onto the surface of the agar immediately after the agar has been coated by the bacterial suspension. When the plate is maintained at room temperature for a period of time before the impregnated disks are placed onto the surface of the agar, the period of time may be about 15, 30, 40 or 60 minutes, or about 1, 1.5, 2, 2.5, 3, 3.5, 4, 4.5, 5, 5.5, 6, or more hours. The plates may also be stored at about 4° C. for up to several days before use, including about 2, 4, 6, 8, 10, 12, 14, 16, 18, 20, 22, 24 or more hours, or 0.5, 1, 1.5, 2, 2.5, 3, 3.5, 4, 4.5, 5, 5.5, 6 or more days.

After the disks are placed on the surface of the agar, the plate may be maintained for a period of time to allow pre-diffusion of the antibiotic, or immediately placed under conditions promoting bacterial growth, such as an incubator under conditions of 5% $CO_2$ and 37° C. If maintained to allow pre-diffusion, the plates may be maintained at room temperature, or at a temperature that is higher or lower than room temperature, such as a centigrade temperature of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or 37 degrees, or a range of temperatures. In one embodiment, the plates are maintained at about 4° C. for a period of time to allow pre-diffusion of the antibiotic. When the plate is maintained for a period of time after the impregnated disks are placed onto the surface of the agar to allow pre-diffusion of the antibiotic, the period of time may be about 15, 30, 40 or 60 minutes, or about 1, 1.5, 2, 2.5, 3, 3.5, 4, 4.5, 5, 5.5, 6, or more hours. As an example, the impregnated disks are placed onto the surface of the agar immediately after the agar has been coated by the bacterial suspension and the plates are placed under conditions promoting bacterial growth. As a further example, the impregnated disks are placed onto the surface of the agar immediately after the agar has been coated by the bacterial suspension, and the plates are maintained at about 4° C. for about 3 hours to allow pre-diffusion before being placed under conditions promoting bacterial growth.

The particular conditions promoting growth of the bacteria will depend on the identity of the bacterial strain being tested. However, appropriate conditions include an incubator under conditions of about 5% $CO_2$ and about 37° C. The skilled artisan will understand that $CO_2$ concentration and temperature can vary.

The plates will be maintained under the conditions promoting growth of the bacteria for a period of time that permits growth of bacterial on the plate to a sufficient degree that the growth can be detected visually, such as by the unaided human eye. The amount of time required to achieve such growth will depend on the identity of the bacterial strain being tested. In general, the amount of time required will be about 8, 16, 24, 32, 40, 48, 56, 64, 72, 80 or more hours.

The zone of inhibition of bacterial growth around the disk on the agar plate can be measured by a variety of suitable means, any of which will reveal the size of the zone of inhibition. For example, a ruler and the unaided human eye may be used to measure the diameter of the zone of inhibition. The phrase "zone of inhibition" has the standard meaning ascribed to the phrase in field of microbiology, and generally refers to the clear region around the paper disk, where antibiotic diffusing from the disk has prevented bacterial growth. Generally, there is a direct correlation between the size of the clear area (the zone of inhibition) and the susceptibility of the bacterium to the antibiotic; the larger the clear area, the more susceptible the bacterium is to the antibiotic. Zones of inhibition that may be realized using the methods of the present invention will vary based on factors that include the identity of the bacteria, the amount of the antibiotic in the disk and the culture conditions. However, the methods of the present invention can be used to produce zones of inhibition measuring at least about 15 mm, at least about 16 mm, at least about 17 mm, at least about 18 mm, at least about 19 mm, at least about 20 mm, at least about 21 mm, at least about 22 mm, at least about 23 mm, and at least about 24 mm, or about 15 mm, about 16 mm, about 17 mm, about 18 mm, about 19 mm, about 20 mm, about 21 mm, about 22 mm, about 23 mm, about 24 mm, about 25 mm or more.

The bacteria that may be tested using the disk diffusion assays of the present invention may be any that are potentially susceptible to the particular antibiotic being assayed. With respect to glycopeptide antibiotics, such bacteria include Gram-positive bacteria such as: *Staphylococcus aureus* (methicillin-susceptible and -resistant strains; vancomycin-susceptible, -intermediate and -resistant strains; heterogenous vancomycin-intermediate strains), *Streptococcus pyogenes*, *Streptococcus agalactiae*, *Streptococcus anginosus* grp. (including *S. anginosus*, *S. intermedius*, and *S. constellatus*), *Streptococcus dysgalactiae* (including *S. dysgalactiae* subsp. *equisimilis*), *Streptococcus pneumoniae*, *Streptococcus* species, including *Streptococcus* Group A species, *Streptococcus* Group B species, *Streptococcus* Group C species, and *Streptococcus* Group D species, *Enterococcus* species, *Enterococcus faecalis* (vancomycin-susceptible and -resistant strains), *Enterococcus faecium* (vancomycin-susceptible and -resistant strains), *Staphylococcus epidermidis* (methicillin-susceptible and -resistant strains), *Staphylococcus haemolyticus*, all strains, species and subspecies of *Clostridium difficile*, including, for example, *C. difficile* PCR ribotypes 001, 106 and 027, and vegetative and spore forms of *Bacillus anthracis*.

The disk diffusion assays of the present invention, and the results obtained therefrom, can be useful in a variety of manners. For example, the assays can be used to determine the effectiveness of a glycopeptide antibiotic, such as oritavancin, against a particular strain of bacteria, whether tested alone or against a known comparator strain. The information gathered from the assay can be used, for example, to guide treatment decisions in an animal, such as a human, that is infected by the bacteria. Treatment decisions may include which glycopeptide antibiotic, such as oritavancin, should be used in treating an infection, the amount of glycopeptide antibiotic to administer to the animal, and the duration of treatment. The disk diffusion assays of the present invention can therefore be used in conjunction with methods of treating an animal, such as a human, with a glycopeptide antibiotic, such as oritavancin.

The disk diffusion assays of the present invention can be performed in medical settings, such as a hospital laboratory, clinic or doctor's office, and the information obtained from the assays can be used as the basis for treatment decisions. For example, the health care provider can follow one or more of the following steps: (a) examine a patient that may have a bacterial infection, (b) obtain a biological sample from the patient, (c) request that a disk diffusion assay of the present invention be conducted on the sample, (d) review the results of the assay to determine whether a glycopeptide antibiotic, such as oritavancin, will be effective if administered to the patient, (e) make a treatment decision based on the results of the assay. The additional step (f) of administering to the patient a glycopeptide antibiotic, such as oritavancin, can be included.

Given the increased incidence of bacterial resistance, it is contemplated that the product label included with a commercial container of the glycopeptide antibiotic, such as oritavancin, can include directions to conduct a disk diffusion assay of the present invention prior to administration of the glycopeptide antibiotic to a patient. By suggesting or requiring that the assay be conducted, the health care provider can be assured that the drug is appropriate for treatment of the particular infection of the patient.

EXAMPLES

Example 1

Test Articles

Oritavancin powder (lot 11953CB00) was from The Medicines Company. P80 (catalog number P5188-100ML, lot # MKBF7194V) and (2-hydroxypropyl)-β-cyclodextrin (catalog number 332593-25G) were from Sigma-Aldrich (Saint Louis, Mo., USA). Cation-adjusted Mueller Hinton agar (catalog number 211438) was obtained from Becton Dickinson and Company (Sparks, Md.).

Test Strains

Bacterial strains used in this study included the methicillin-susceptible *Staphylococcus aureus* (MSSA) quality control strain used in the disk diffusion assay ATCC 25923, the CLSI quality control BMD MIC isolate MSSA ATCC 29213, methicillin-resistant *S. aureus* (MRSA) NRS123, heterogenous vancomycin-intermediate *S. aureus* (hVISA) NRS2, vancomycin-intermediate *S. aureus* (VISA) NRS3, VISA ATCC 700699, VISA NRS402, MRSA U206056 and MSSA T972018 (the latter two isolates were obtained from Covance, Indianapolis, Ind.). Two *S. aureus* isolates exhibiting reduced susceptibility to oritavancin, which were derived in-house from 20 rounds of daily exposure to oritavancin, were also used in the study.

Study Design

The study was designed to identify conditions that improve oritavancin diffusion in agar and consequently yield a zone diameter ≥15 mm for the CLSI quality control strain MSSA ATCC 25923. Excipients that increased the disk diffusion of oritavancin in agar relative to disks containing only oritavancin were identified and selected for further study. Concentrations of excipients that maximized diffusion but did not affect bacterial growth were evaluated. Batches of disks with optimized disk content were prepared and used to determine if zone diameters could be distinguished amongst selected *S. aureus* isolates exhibiting a range of MICs that had been previously determined by the broth microdilution method. A prediffusion step at room temperature was introduced to maximize oritavancin diffusion prior to initiation of bacterial growth. In this step, the antimicrobial disks were placed on agar plates seeded with a bacterial isolate and incubated at room temperature for 3 hours. Plates were then incubated overnight at 37° C. Zone diameters around the disks in which bacterial growth was inhibited were measured with a ruler and reported in millimeters.

Experimental Procedures

Oritavancin powder was dissolved in freshly-prepared filter-sterilized P80 (ranging between 0.002% and 10%) or (2-hydroxypropyl)-β-cyclodextrin (HPCD; 10%) at concentrations between 4.5 and 18 mg/ml (adjusted for potency based on lot purity). Ethanol-sterilized Whatman paper disks (6 mm diameter) were allowed to dry then impregnated with 20 microliters of oritavancin solution containing total amounts ranging from 90 to 360 micrograms. Disks were allowed to dry at room temperature for various times prior to use.

Bacterial suspensions were prepared and adjusted to an optical density of 0.1 at 600 nm. Standard cation-adjusted Mueller Hinton agar plates (90 mm diameter) were seeded with bacterial suspensions by initially swabbing the center of plate then moving outward towards the edge. The plate was swabbed a second time, perpendicular to the orientation of the first swab. To assess the impact of prediffusion on diameter of inhibition zones, two disks were immediately placed on one half of the plate and the plate was incubated for 3 hours at room temperature. After 3 hours, two additional disks were placed on the other half of the plate then the plate was incubated overnight at 37° C. Zone diameters were measured with a ruler and reported in millimeters.

Results

Three conditions were identified that promoted diffusion of oritavancin in agar and resulted in zone diameters of ≥15 mm for the quality control strain *S. aureus* ATCC 25923.

1) Prediffusion increases zone diameters. An initial experiment was performed to determine if a prediffusion step would increase zone diameters. Disks containing 360 µg of oritavancin dissolved in 0.002% P80 were prepared and placed on plates seeded with bacteria. Following incubation at room temperature for 3 hours to allow for prediffusion, the plates were then placed at 37° C. overnight. An average zone diameter without prediffusion produced by two disks was 10.5 mm against MSSA ATCC 25923 (FIG. 1A). The average zone diameter increased to 12 0 mm when prediffusion for 3 hours was permitted (FIG. 1C). Although zones of clearance with the prediffusion step were below the 15 mm diameter minimum threshold recommended by CLSI for adequate disk diffusion assay performance, prediffusion increased the area of the zone of clearance by approximately 24% and was therefore incorporated in further testing.

2) Inclusion of 5% P80 as an excipient increases zone diameters. As shown in FIG. 1, the average zone diameter resulting from two disks prepared with oritavancin dissolved in 5% P80 solution against the quality control strain MSSA ATCC 25923 was 14.8 mm (B) and increased to 17.0 mm when prediffusion was performed (D). Further testing of excipients revealed that 10% HPCD ((2-hydroxypropyl)-β-cyclodextrin) also improved diffusion of oritavancin in agar (Table 1). However, only disks prepared with oritavancin dissolved in 5% P80 but not 10% HPCD exhibited zone diameters that varied according to the strain broth microdilution MIC (Table 1). Therefore, only disks containing oritavancin dissolved in 5% P80 were used in subsequent experiments.

TABLE 1

Effect of excipients on zone diameters for *S. aureus* isolates

| Strain | Pheno-type | Oritavancin BMD MIC (µg/ml) | Average zone diameter[a] (mm ± SD) for disks containing 360 µg oritavancin Excipient | |
|---|---|---|---|---|
| | | | 5% P80[b] | 10% HPCD[c] |
| ATCC 25923 | MSSA | 0.125 | 19.0 | 17.5 |
| NRS2 | hVISA | 0.25 | 17.8 | 17.5 |
| ATCC 700699 | VISA | 1 | 15.0 | 17.3 |
| NRS3 | VISA | 1 | 14.0 | 16.8 |
| NRS402 | VISA | 1 | 14.8 | 17.5 |

[a]The reported zone diameters were from disks that had undergone the 3 hour prediffusion step. Results are from the average of 2 disks.
[b]Disks prepared from oritavancin dissolved in 5% P80 were stored at room temperature for 5 days prior to use.
[c]Disks prepared from oritavancin dissolved in 10% HPCD were made the same day of use.

The effect of 5% P80 on diffusion of other antimicrobial agents was examined. Disks containing 30 µg of daptomycin, telavancin or vancomycin without (control) or with 5% P80 were prepared. As shown in Table 2, addition of 5% P80 to disks containing 30 µg of the lipoglycopeptide telavancin increased zone diameters by an average of 1 5 mm against MSSA ATCC 25923. Inclusion of 5% P80 had no effect on zone diameters of daptomycin and vancomycin.

TABLE 2

Effect of 5% P80 on zone diameters obtained with various antimicrobial agents

| Antimicrobial agent | Amount in disk (µg) | Average zone diameter (mm) obtained with *S. aureus* ATCC 25923[a] | |
|---|---|---|---|
| | | Control | +5% P80 |
| Daptomycin | 30 | 18.5 | 18 |
| Telavancin | 30 | 16.5 | 18 |
| Vancomycin | 30 | 17.5 | 17.5 |

[a]Results are from the average of 2 disks without prediffusion.

3) Storage of prepared disks at room temperature before use increases zone diameters. Zone diameters were noted to increase when disks prepared from oritavancin dissolved in 5% P80 were incubated at room temperature for periods longer than one day prior to use. As shown in Table 3, zone diameters increased as the time elapsed between disk preparation and use. From these results, disks were stored at room temperature for at least 8 days before use.

TABLE 3

Effect of storage of disks at room temperature prior to use on zone diameter

| Strain | Average zone diameter[a] (mm) Elapsed time between disk preparation and use[b] | | | | |
|---|---|---|---|---|---|
| | Same day | 1 day | 4 days | 6 days | 8 days |
| ATCC 25923 | 14.0 | 15.0 | 15.8 | 16.3 | 17.0 |

[a]The reported zone diameters were from disks that had undergone the 3-hour prediffusion step. Results are from the average of 2 disks.
[b]Disks were prepared from a single stock solution of 18 mg/ml oritavancin dissolved in 5% P80. Disks were stored at room temperature until tested.

Using the optimal conditions described above (inclusion of 5% P80, 3 hour prediffusion and drying of disks at least 8 days before use), experiments were performed to determine if *S. aureus* isolates of differing BMD MICs could be distinguished by zone diameter in disk assays. For these experiments, disks containing 360 µg oritavancin in 5% P80 were prepared and stored at room temperature for 8 and 14 days before use. As shown in Table 4, zone diameters diminished for isolates exhibiting increased BMD MIC to oritavancin. A correlation between zone diameter and BMD MIC for all the isolates tested was evident (r=−0.78) and the correlation improved when the two laboratory-selected oritavancin reduced-susceptibility isolates were excluded from the analysis (r=−0.94): zone diameters for the two reduced-susceptibility isolates of *S. aureus* were approximately 2 mm smaller compared to MSSA and MRSA isolates exhibiting the same BMD MICs. Prediffusion increased zone diameters for MSSA and MRSA strains by an average of approximately 2.5 mm Similarly, prediffusion increased zone diameters for the VISA and oritavancin reduced-susceptibility isolates by an average of approximately 1.1 mm

TABLE 4

Zone diameters for S. aureus isolates exhibiting a range of BMD MICs.

| | | Oritavancin BMD MIC (μg/ml) | Zone diameter (mm ± SD)[a] | | | | | |
|---|---|---|---|---|---|---|---|---|
| | | | Experiment 1[b] | | Experiment 2[c] | | | |
| | | | | | No | | Average | |
| Strain | Phenotype | | No prediffusion[d] | Prediffusion[e] | prediffusion | Prediffusion | No prediffusion | Prediffusion |
| NRS123 | MRSA | 0.03 | 16.3 ± 0.4 | 19.5 ± 0.0 | 15.8 ± 0.4 | 18.0 ± 0.0 | 16.0 ± 0.4 | 18.8 ± 0.9 |
| ATCC 29213 | MSSA | 0.06 | 15.8 ± 0.4 | 18.3 ± 0.4 | n.d. | n.d. | 15.8 ± 0.4 | 18.3 ± 0.4 |
| NRS121 | MRSA | 0.06 | n.d. | n.d. | 15. ± 0.0 | 17.3 ± 0.4 | 15. ± 0.0 | 17.3 ± 0.4 |
| ATCC 25923 | MSSA | 0.12 | 15.3 ± 0.4 | 18.0 ± 0.0 | 14.5 ± 0.0 | 17.0 ± 0.0 | 14.9 ± 0.5 | 17.5 ± 0.6 |
| U206056 | MRSA | 0.25 | 15.5 ± 0.0 | 17.8 ± 0.4 | 14.5 ± 0.0 | 17.0 ± 0.0 | 15.0 ± 0.6 | 17.4 ± 0.5 |
| NRS2 | hVISA | 0.25 | 15.5 ± 0.0 | 17.5 ± 0.0 | 14.3 ± 0.4 | 17.0 ± 0.0 | 14.9 ± 0.8 | 17.3 ± 0.3 |
| NRS123-ORI[RS] | MRSA | 0.25 | n.d. | n.d. | 14.0 ± 0.0 | 15.0 ± 0.0 | 14.0 ± 0.0 | 15.0 ± 0.0 |
| T972018 | MSSA | 0.5 | 15.5 ± 0.0 | 17.5 ± 0.0 | 14.5 ± 0.0 | 17.3 ± 0.4 | 15.0 ± 0.6 | 17.4 ± 0.3 |
| NRS121-ORI[RS] | MRSA | 0.5 | n.d. | n.d. | 13.0 ± 0.0 | 14.0 ± 0.0 | 13.0 ± 0.0 | 14.0 ± 0.0 |
| ATCC 700699 | VISA | 1 | 13.5 ± 0.7 | 14.5 ± 0.0 | 13.0 ± 0.0 | 14.0 ± 0.0 | 13.3 ± 0.5 | 14.3 ± 0.3 |
| NRS402 | VISA | 1 | 13.3 ± 0.4 | 14.8 ± 0.4 | 13.0 ± 0.0 | 14.3 ± 0.4 | 13.1 ± 0.3 | 14.5 ± 0.4 |

[a]Zone diameters were from disks containing 360 μg of oritavancin in 5% P80.
[b]Disks used in Experiment 1 were stored at room temperature for 14 days before use.
[c]Disks used in Experiment 2 were stored at room temperature for 8 days before use.
[d]Disks were added immediately to the seeded agar plates prior to incubation at 37° C.
[e]Prediffusion consisted of adding disks to seeded plates then incubating at room temperature for 3 hours prior to incubation overnight at 37° C.

Follow-up experiments were performed to determine if disk content could be optimized to better differentiate zone diameters of strains that exhibit BMD MIC between 0.03 and 0.25 μg/ml. Disks containing a range of concentrations of P80 (2.5, 5 and 10%) and oritavancin (90, 180 and 360 μg) were prepared and tested against NRS123 (BMD MIC 0.03 μg/ml) and NRS2 (BMD MIC=0.25 μg/ml). As shown in Table 5, differences in zone diameters between NRS 123 and NRS2 were larger with disks containing 2.5% P80 than with disks containing 5 or 10% P80. Further study of P80 concentration may provide for larger differences in zone diameter for isolates exhibiting BMD MICs around 0.25 μg/ml.

The newly discovered conditions described here for oritavancin produce zone diameters >15 mm for the quality control strain MSSA ATCC 25923 and therefore meet the minimum zone diameter recommended by CLSI for an appropriate disk diffusion assay.

Example 2

Because inclusion of P80 as an excipient in oritavancin antimicrobial disks was found to increase zone diameters to ≥15 mm, incorporation of P80 into Cation-adjusted Mueller-Hinton agar (CAMHA) was tested. As shown in Table 6, zone diameters on CAMHA containing 1% P80 obtained for disks prepared with various concentrations of oritavancin dissolved in 0.002% P80 remained <15 mm, even when 3 h prediffusion was used. Furthermore, CAMHA containing 1% P80 did not increase zone diameters for disks containing 180 μg oritavancin dissolved in 2.5% P80 compared to zone diameters obtained from disks placed on agar without P80 (Table 7). From these results, it was concluded that inclusion of 1% P80 in the agar does not enhance diffusion of oritavancin and does not provide for zone diameters of adequate size (i.e. ≥15 mm)

TABLE 5

Optimization of disk content to distinguish zone diameters of isolates with oritavancin BMD MICs ranging between 0.03 and 0.25 μg/ml.

| | | Average zone diameter (mm) with disks containing indicated amount of oritavancin and P80[a] | | | | | | | | |
|---|---|---|---|---|---|---|---|---|---|---|
| | Oritavancin BMD | 2.5% P80[b] | | | 5% P80[c] | | | 10% P80[c] | | |
| Strain | MIC (μg/ml) | 90 μg | 180 μg | 360 μg | 90 μg | 180 μg | 360 μg | 90 μg | 180 μg | 360 μg |
| NRS123 | 0.03 | 15.8 | 16.5 | 16.8 | 16 | 17.3 | 18.5 | 15.5 | 17.3 | 17.5 |
| NRS2 | 0.25 | 14 | 14.8 | 15 | 15 | 16 | 18 | 15.8 | 16 | 16.5 |
| Difference in diameter (mm)[d] | | 1.8 | 1.7 | 1.8 | 1 | 1.3 | 0.5 | −0.3 | 1.3 | 1 |

[a]Average zone diameter was from 2 disks. Zone diameters are from disks that had undergone prediffusion.
[b]Disks containing 2.5% P80 and the various concentrations of oritavancin were stored for 8 days at room temperature prior to use.
[c]Disks containing 5% and 10% P80 and the various concentrations of oritavancin were stored for 14 days at room temperature prior to use.
[d]Difference in diameter is the result of the zone diameter obtained for NRS2 subtracted from NRS123.

TABLE 6

Zone diameters from oritavancin-containing disks placed on
CAMHA containing 1% P80 are <15 mm against MSSA ATCC 25923.

| Strain | Oritavancin (μg) in disk | P80 content in CAMHA (%) | Average zone diameter (mm)[a] | |
|---|---|---|---|---|
| | | | No prediffusion | Prediffusion |
| MSSA ATCC 25923 | 45 | 1 | 12 | 12.3 |
| MSSA ATCC 25923 | 90 | 1 | 11.8 | 12.8 |
| MSSA ATCC 25923 | 180 | 1 | 12.3 | 13 |
| MSSA ATCC 25923 | 360 | 1 | 12.8 | 12.5 |

[a]Average zone diameters are from duplicate determinations (2 disks). Disks used in this experiment contained the indicated concentrations of oritavancin dissolved in 0.002% P80.

TABLE 7

Zones diameters for oritavancin-containing disks on agar containing
1% P80 are similar to zone diameters obtained on agar without P80.

| Strain | P80 content in CAMHA (%) | Zone diameter (mm)[a] | |
|---|---|---|---|
| | | No prediffusion | Prediffusion |
| MSSA ATCC 29213 | 0 | 15.3 | 18.3 |
| MSSA ATCC 29213 | 1 | 15.3 | 18 |

[a]Average zone diameters are from duplicate determinations (2 disks). Disks used in this experiment contained 180 μg oritavancin dissolved in 2.5% P80.

Example 3

The experiment described in Example 1 was repeated under identical conditions with the exception that the prediffusion step was conducted at 4° C. for 3 or 6 hours. As shown in Table 8, prediffusion for 6 hours and at 4° C. increased the inhibition zone diameters obtained for MSSA ATCC 25923 compared to prediffusion for 3h or at room temperature, respectively.

TABLE 8

Effect of prediffusion temperature and
time on inhibition zone diameter.

| | Inhibition zone diameter (mm)[a] resulting from prediffusion at: | | | |
|---|---|---|---|---|
| | Room temperature | | 4° C. | |
| Strain | 3 h | 6 h | 3 h | 6 h |
| ATCC 25923 | 16.5, 17 | 18, 18.5 | 18, 19 | 21, 22 |

[a]Inhibition zone diameters from duplicate determinations are shown. Disks used in this experiment were impregnated with 20 μl of 9 mg/ml oritavancin dissolved in 2.5% P80.

In the next experiments, blank paper disks from Oxoid (catalog #CT0998B) were also tested as they represent a commercially-available source of antibiotic disks. As shown in Table 9, inhibition zone diameters obtained with Oxoid disks impregnated with oritavancin solutions were smaller compared to those obtained with disks prepared from Whatman #5 paper, perhaps owing to the increased thickness of the Oxoid disks relative to the Whatman #5 paper.

TABLE 9

The effect of disk type on inhibition zone
diameters obtained for MSSA ATCC 25923.

| Oritavancin in disk (μg) | % P80 in Oritavancin solution | Inhibition zone diameter (mm) obtained for MSSA ATCC 25923 according to disk type[a] | |
|---|---|---|---|
| | | Whatman #5 | Oxoid |
| 180 | 2.5 | 15.5, 16 | 12.5, 12.5 |
| 270 | 2.5 | 15.5, 15.5 | 13, 13 |
| 360 | 2.5 | 15.5, 15.5 | 13, 13 |
| 180 | 5 | 14.5, 14.5 | 12, 12.5 |
| 270 | 5 | 16, 16 | 13, 13.5 |
| 360 | 5 | 16, 16.5 | 14, 14 |

[a]Inhibition zone diameters from duplicate determinations are shown. Disks used in this experiment were impregnated with 20 μl of oritavancin solution dissolved in the indicated P80 concentration. Disks were stored at room temperature for 7 days prior to use. Prediffusion was for 3 h at 4° C.

Oxoid disks containing 360 μg oritavancin in 5% P80 were selected for further study but were stored at room temperature for 30 days before use and 6 hours of prediffusion at 4° C. was used with the intent of increasing inhibition zone diameters. As shown in Table 10, inhibition zone diameters were >15 mm for MSSA ATCC 25923 and varied according to the oritavancin BMD MIC of the S. aureus isolates tested.

TABLE 10

Inhibition zone diameters for S. aureus isolates
using oritavancin-impregnated Oxoid disks.

| Strain | Phenotype | Oritavancin BMD MIC (μg/ml) | Inhibition zone diameter (mm)[a] |
|---|---|---|---|
| ATCC 25923 | MSSA | 0.12 | 17.5 |
| NRS2 | hVISA | 0.25 | 16.5 |
| Mu50 | VISA | 1 | 13 |

[a]Disks used in this experiment were impregnated with 20 μl of 18 mg/ml oritavancin dissolved in 5% P80. Disks were incubated for 30 days at room temperature prior to use. Prediffusion was for 6 hours at 4° C.

Example 4

Alternative excipients in which oritavancin was dissolved were investigated including a mixture of both P80 and Span 80 and the surfactants Merpol S E, Brij 30 and poly(ethylene glycol)sorbitol hexaoleate.

TABLE 11

| Test articles | |
|---|---|
| Test article | Supplier |
| Oritavancin diphosphate (lot # 87556IL00) | The Medicines Company, Parsippany, NJ, USA |
| Antimicrobial susceptibility test discs-blank discs (catalog # CT0998B) | Oxoid Ltd., Basingstoke, UK. |
| P80 (catalog # P5188-50ML, lot# MKBF7194V) | Sigma-Aldrich, Saint Louis, MO, USA |
| Span 80 (catalog # S6760-250ML, lot# MKBF1605V) | Sigma-Aldrich, Saint Louis, MO, USA |
| Merpol SE surfactant (catalog # 421340-250ML, batch # 03211CG) | Sigma-Aldrich, Saint Louis, MO, USA |

TABLE 11-continued

Test articles

| Test article | Supplier |
| --- | --- |
| Brij 30 (catalog # 235989-100ML, lot # MKBG9120V) | Sigma-Aldrich, Saint Louis, MO, USA |
| Poly(ethylene glycol) sorbitol hexaoleate (catalog # 466409-1L, lot # MKBH9590V) | Sigma-Aldrich, Saint Louis, MO, USA |
| Cation-adjusted Mueller Hinton agar (catalog # 211438) | Becton Dickinson and Company, Sparks, MD, USA |
| Sterile calcium alginate swabs (catalog # 25-806 2PA) | Puritan Medical Products Company, LLC, Guilford, ME, USA. |
| Cotton tip swabs (reference # 89031-270) | VWR International, LLC., Radnor, PA, USA |
| Sterile polyester fiber tipped swabs (catalog # 14-959-90) | Fisher Scientific, Ottawa, ON, Canada |
| Sterile cotton swabs (reference # 25-806 1PC) | Puritan Medical Products Company, LLC, Guilford, ME, USA. |
| Sterile polyester swabs (reference # 25-806 1PD) | Puritan Medical Products Company, LLC, Guilford, ME, USA. |
| Sterile rayon swabs (reference # 25-806 1PR) | Puritan Medical Products Company, LLC, Guilford, ME, USA. |
| Sterile foam swabs (reference # 25-1506 1PF) | Puritan Medical Products Company, LLC, Guilford, ME, USA. |
| Sterile flocked swabs (reference # 25-3406 1PN) | Puritan Medical Products Company, LLC, Guilford, ME, USA. |

Test Strains

Bacterial strains used in this study included the methicillin-susceptible *Staphylococcus aureus* (MSSA) quality control strain ATCC 25923, the quality control BMD MIC isolate MSSA ATCC 29213, methicillin-resistant *S. aureus* (MRSA) ATCC 33591, the Network on Antimicrobial Resistance in *S. aureus* isolates heterogenous vancomycin-intermediate *S. aureus* (hVISA) NRS2, hVISA NRS36, vancomycin-intermediate *S. aureus* (VISA) Mu50 (ATCC 700699), VISA NRS3 and VISA NRS402, and clinical isolates from the phase 2 study SIMPLFI (8) clinical isolates (obtained from Covance, Indianapolis, Ind., USA) MRSA U206056, MSSA Q141066, MRSA Q670505, MSSA 5815246, MSSA T759545, MRSA T998528, MSSA U148267, MSSA U781969, MSSA U933236, MRSA V257345, MRSA V406957, MRSA Q141067, MRSA Q670607, MSSA 5815247, MSSA T811355, MRSA T998608, MRSA U260847, MRSA U784439, MRSA U933237, MRSA V288615 and MSSA V406985.

Study Design

The emulsifying agent Span 80 was added to P80 as a second excipient and a variety of ratios of P80:Span80 were investigated in an effort to eliminate both the need to store disks for 30 days prior to use and the prediffusion step. Concentrations and ratios of excipients that maximized diffusion but did not affect bacterial growth were evaluated. Batches of disks with optimized drug and excipients were prepared. These optimized disks were used to determine whether selected *S. aureus* clinical and reference isolates exhibiting a range of BMD MICs could be distinguished on the basis of their inhibition zone diameters.

Experimental Procedures

Owing to their high viscosity, P80 and Span 80 liquids were transferred to 15 ml Falcon snap cap tubes by pipetting and allowing the volumes of the liquid to fully drain from the pipette before mixing. P80 and Span 80 were mixed thoroughly by extensive tilting and rotation of the tubes. P80/Span 80 mixtures were thereafter diluted with sterile water to achieve a total excipient concentration of 1 to 4% (vol/vol). Merpol SE and Brij 30 solutions were prepared in sterile water at 5% (vol/vol). A solution of poly(ethylene glycol) sorbitol hexaoleate was prepared in sterile water at 1% (vol/vol).

The hydrophile-lipophile balance (HLB) numbers of the various P80/Span 80 mixtures were calculated using the equation: HLB XY=HLB X (% X)+HLB Y (% Y). For example, the HLB of a 1:1 (vol/vol) mixture of P80 (HLB=15)/Span 80 (HLB=4.3) is 15(0.5)+4.3(0.5)=9.7.

Oritavancin powder was dissolved in freshly-prepared solutions of the indicated excipients at concentrations of 0.625, 1.25, 2.5, 5, and 10 mg/ml (adjusted for potency based on lot 875561L00 purity of 83.1%) by vortexing for a minimum of 5 minutes. Oritavancin solutions in the various excipients, while not visually clear, were free from any apparent particulates as assessed visually. Sterile Oxoid blank disks were impregnated with 20 µl of these oritavancin solutions, resulting in oritavancin disk loads ranging from 12.5 to 200 µg. Unless indicated otherwise, disks were allowed to dry overnight at room temperature prior to use.

Bacterial suspensions from isolated colonies on overnight cation-adjusted Mueller Hinton agar plates were prepared in sterile saline and adjusted to an optical density of 0.1 at 600 nm Standard cation-adjusted Mueller Hinton agar plates (90 mm diameter) were seeded with bacterial suspensions by initially swabbing the center of plate then moving outward. Swabbing was continued at a right angle and then at an oblique angle to the first and second swabs. Disks were placed upon the seeded plates with sterile forceps. Plates were then incubated overnight at 37° C. and inhibition zone diameters were measured with a ruler and reported in millimeters.

Results

A series of experiments were performed to assess the impact of the following parameters upon the inhibition zone diameters and other attributes of the inhibition zone that could potentially contribute to variability in assessing the zone diameter, such as margin, concentricity and degree of clearing: 1) the total excipient concentration in the oritavancin solution, 2) the ratio of P80/Span 80 in the oritavancin solution, 3) the oritavancin disk load and type of swab used for seeding and 4) other surfactants with similar HLB numbers. Each set of related experiments and their results are further described below.

1) Total excipient concentration in the oritavancin solution. As a benchmark, oritavancin was dissolved at 2.5 mg/ml in solutions containing 0.5 to 4% P80/Span 80 (at a ratio of 35:65 vol/vol). Disks containing 25 µg oritavancin in 4% P80/Span 80 were prepared and allowed to dry for approximately 3 hours at room temperature. As shown in Table 12, increasing the percentage of the P80/Span 80 mixture in solution from 0.5 to 4% increased the inhibition zone diameter. Based on these findings, a 4% solution of P80/Span 80 was used for further testing. However, inhibition zones under all tested conditions were not fully concentric and they had jagged edges, resulting in the need to estimate the diameter of the inhibition zones. It was noted that the agar surface was visibly scratched by the polyester-tipped swabs used when seeding with bacteria; hence, swab type was identified as another variable to be explored during optimization (results presented further below).

TABLE 12

Effect of total excipient concentration (as percent of P80/Span 80 in water) on inhibition zone diameter.

| Oritavancin disk content[a] (μg) | Percent P80/Span 80 in water | Inhibition zone diameter[b] for MSSA ATCC 25923 (mm) |
|---|---|---|
| 50 | 0.5 | 10 |
| 50 | 1 | 15 |
| 50 | 2 | 20 |
| 50 | 4 | 28 |

[a]Disks were impregnated with 20 μl of a 2.5 mg/ml solution of oritavancin dissolved in the indicated percentage of P80/Span 80 mixture (35:65) and allowed to dry for approximately 3 hours at room temperature before use.
[b]Inhibition zone diameters were not fully concentric and lacked a defined margin and therefore estimates of the diameter are shown.

2) Ratio of P80/Span 80 in the oritavancin solution. Preliminary benchmark testing comparing P80/Span 80 ratios (vol/vol) of 20:80, 35:65 and 50:50 revealed that a 50:50 (1:1) ratio resulted in larger inhibition zones (data not shown). The ratio of P80/Span 80 was further varied to determine the proportion that results in the largest inhibition zone diameters. Different ratios of P80/Span 80 (vol/vol) were prepared as indicated and used to dissolve oritavancin powder at a concentration of 2.5 mg/ml in 4% (vol/vol) excipient solution. Disks were impregnated with 20 μl of the solutions and allowed to dry overnight before use. As shown in Table 13, varying the ratio of P80/Span 80 substantially affected the inhibition zone diameter. The optimal ratio of P80/Span 80 was determined to be 1:1 (vol/vol). Similar to the finding that is noted above, the inhibition zones were not concentric since polyester-tipped swabs were also used in this experiment.

TABLE 13

Effect of P80/Span 80 ratio on inhibition zone diameter versus S. aureus isolates.

| S. aureus isolate | Phenotype | Oritavancin BMD MIC (μg/ml) | Oritavancin disk content (μg) | Inhibition zone diameter (mm)[a] obtained with disks containing 4% of the indicated P80/Span 80 ratio | | | | |
|---|---|---|---|---|---|---|---|---|
| | | | | 50:50 | 60:40 | 70:30 | 80:20 | 90:10 |
| ATCC 25923 | MSSA | 0.06 | 50 | 23 | 21 | 19 | 16 | 13 |
| NRS2 | hVISA | 0.25 | 50 | 16 | 15 | 14 | 14 | 12 |
| Mu50 | VISA | 1 | 50 | 10 | 11 | 12 | 12 | 12 |

[a]Disks were impregnated with 20 μl of a 2.5 mg/ml solution of oritavancin dissolved in 4% of the indicated P80/Span 80 ratio and allowed to dry overnight at room temperature before use. Inhibition zone diameters were not fully concentric and lacked a defined margin and therefore estimates of the diameter are shown.

3) Oritavancin disk load and swab type. The following experiments were performed to optimize oritavancin disk content and to determine if swab type could affect the shape and margin of the inhibition zone, with a desired result to be a more concentric zone with a defined margin. Solutions of oritavancin ranging from 0.625, 1.25, 2.5, 5 to 10 mg/ml in 4% P80/Span 80 (1:1 vol/vol) in water were used to prepare disks containing 12.5, 25, 50, 100 and 200 μg of oritavancin, respectively. Disks were dried overnight at room temperature.

Figure 2:
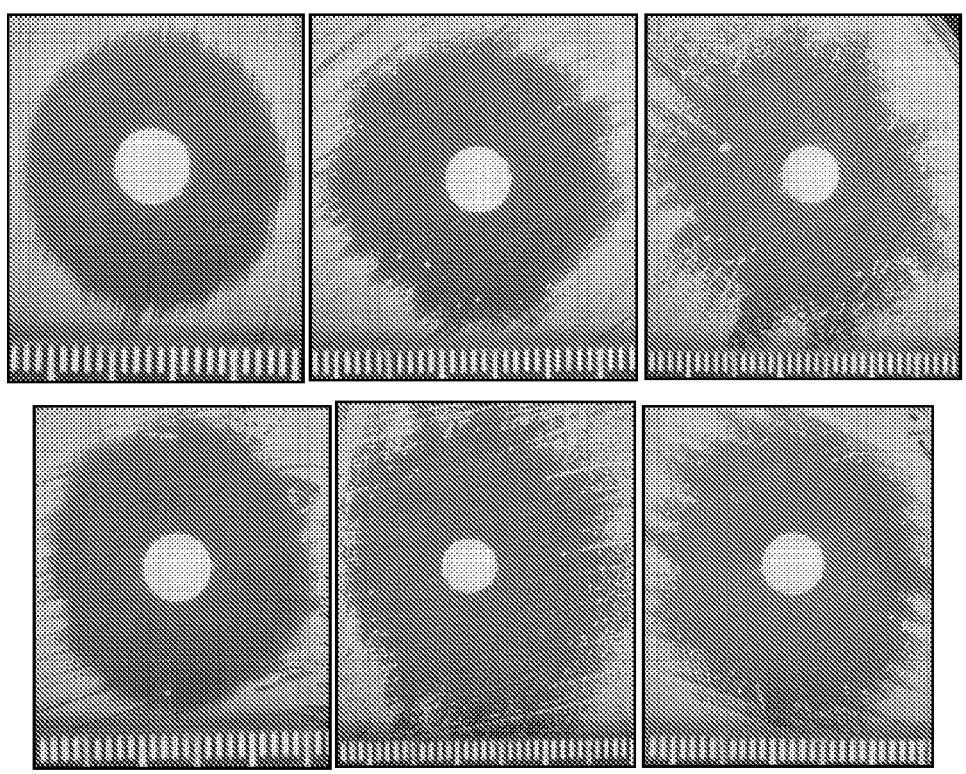
FIG. 2 shows the effect of swab type on inhibition zone diameter obtained with oritavancin disks against MSSA ATCC 25923. Disks were impregnated with 20 μl of 1.25 mg/ml oritavancin solution in 4% P80/Span 80 (1:1 vol/vol) and allowed to dry overnight before use. Top left panel, calcium alginate swab, inhibition zone diameter=21 mm; top middle panel, cotton swab, inhibition zone diameter=approx. 24 mm; top right panel, polyester swab, inhibition zone diameter=approx. 24 mm; bottom left panel, rayon swab, inhibition zone diameter=approx. 22 mm; bottom middle panel, foam swab, inhibition zone diameter=approx. 26 mm; bottom right panel, flocked swab, inhibition zone diameter=approx. 24 mm The ruler measurement is in millimeters.

As shown in Table 14, inhibition zone diameters for MSSA ATCC 25923 and hVISA NRS2 were the largest at a disk content of 25 μg oritavancin and subsequently declined with increasing amounts, likely indicating an important interaction between oritavancin and the surfactant blend. Inhibition zone diameters varied according to the BMD MIC of the S. aureus isolates tested. Calcium alginate swabs produced concentric inhibition zones (and almost no visually-perceptible effect on the agar surface) with only modestly smaller diameters compared to zones obtained with cotton swabs (FIG. 2, top left panel). From this experiment, an oritavancin disk content of 25 μg was selected for further evaluation since it yielded inhibition zone diameters that could discriminate amongst strains with a range of oritavancin MICs as determined by BMD. Seeding of the agar with calcium alginate swabs was also found to result in concentric inhibition zones and hence calcium alginate swabs were selected for further study.

TABLE 14

Effect of oritavancin disk content and swab type on inhibition zone diameters versus S. aureus isolates.

| Oritavancin disk content[a] (μg) | Inhibition zone diameter (mm) | | | | | |
|---|---|---|---|---|---|---|
| | Calcium alginate swab[b] | | | Cotton swab[c] | | |
| | 25923 | NRS2 | Mu50 | 25923 | NRS2 | Mu50 |
| 12.5 | 20 | 12.5 | no zone | 27 | 13 | no zone |
| 25 | 21 | 16 | no zone | 30 | 17 | 7 |
| 50 | 19 | 15 | 7 | 24 | 17 | 10 |
| 100 | 14 | 11 | 8 | 21 | not done | 11 |
| 200 | 11 | 10 | 8 | 15 | 13 | 10 |

[a]Oritavancin solutions in 4% P80/Span 80 (1:1 (vol/vol)) were prepared at concentrations of 0.625, 1.25, 2.5, 5 and 10 mg/ml. Disks were impregnated with 20 μl with the solutions and allowed to dry overnight at room temperature before use.
[b]Inhibition zone diameters obtained with the calcium alginate swabs were concentric.
[c]Inhibition zone diameters were not fully concentric and lacked a defined margin and therefore estimates of the diameter are shown.

A number of different swab types were tested to determine if other types would result in concentric inhibition zones comparable with those obtained with the calcium alginate swabs. A solution of 1.25 mg/ml oritavancin in 4% P80/Span 80 (1:1 vol/vol) was used to prepare disks with a final amount of 25 μg oritavancin/disk. Disks were dried overnight at room temperature before use. As shown in FIG. 2, swab type dramatically affected the inhibition zone diameter and shape, as most clearly seen by zones obtained with the polyester (top right panel) and foam swabs (bottom middle panel). The calcium alginate swabs resulted in concentric inhibition zones that were easily measurable (21 mm; top left panel). Another alternative may be rayon swabs, resulting in an inhibition zone diameter of approx. 22 mm and a near-concentric zone (bottom left panel). The results show that calcium alginate swabs and possibly rayon swabs (catalog numbers 25-806 2PA and 25-806 1PR, respectively; Puritan Medical Products Company, LLC) provide for concentric zones and should be used for seeding of bacteria in the oritavancin disk diffusion assay.

4) Surfactants with similar HLB numbers to the 1:1 (vol/vol) mixture of P80/Span 80. Other surfactants with a hydrophile-lipophile balance (HLB) number comparable to that of the 1:1 (vol/vol) mixture of P80/Span 80 (HLB number=9.7) were tested to determine if they could promote diffusion of oritavancin in agar similar to the 1:1 (vol/vol) P80/Span 80 mixture. Oritavancin powder was dissolved at 1.25 mg/ml in either 5% Merpol SE (HLB number=10), 5% Brij 30 (HLB number=9) or 1% poly(ethylene glycol) sorbitol hexaoleate (HLB number=10). Disks were impregnated with 20 µl of the above solutions and dried overnight at room temperature. As shown in Table 15, the surfactants Merpol SE, Brij 30 and poly(ethylene glycol)sorbitol hexaoleate did not result in inhibition zone diameters that were above the minimum acceptable cutoff (15 mm) indicated by CLSI for MSSA ATCC 25923. Thus, these agents were not further pursued.

TABLE 15

Inhibition zone diameters obtained with other surfactants against S. aureus isolates.

| S. aureus isolate | Inhibition zone diameter (mm) | | |
|---|---|---|---|
| | 5% Merpol SE[a] | 5% Brij 30[b] | 1% poly(ethylene glycol) sorbitol hexaoleate[c] |
| ATCC 25923 | 10 | 8 | 9 |
| NRS2 | 11 | 8 | 9 |
| Mu50 | 9 | no zone | 8 |

[a]Discs were impregnated with 20 µl of a solution of 1.25 mg/ml oritavancin dissolved in 5% Merpol SE.
[b]Discs were impregnated with 20 µl of a solution of 1.25 mg/ml oritavancin dissolved in 5% Brij 30.
[c]Discs were impregnated with 20 µl of a solution of 1.25 mg/ml oritavancin dissolved in 1% poly(ethylene glycol) sorbitol hexaoleate.

Figure 3:
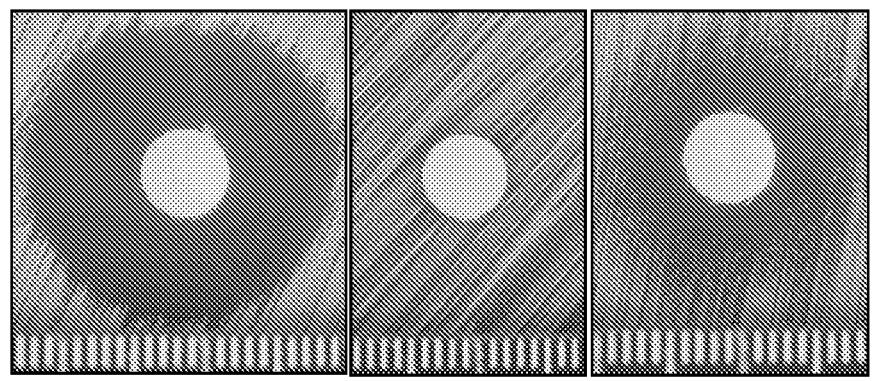
FIG. 3 shows inhibition zone diameters against MSSA ATCC 25925 (left panel), VISA Mu50 (middle panel) and hVISA NRS2 (right panel). Disks were impregnated with 20 μl of 1.25 mg/ml oritavancin solution in 4% P80/Span 80 (1:1 [vol/vol]) and allowed to dry overnight before use. Note the individual colonies surrounding the clear inhibition zone for the NRS2 isolate (right panel). The ruler measurement is in millimeters.

5) Validation of the oritavancin disk diffusion assay. An expanded series of S. aureus isolates with various phenotypes was tested to determine if inhibition zone diameters would vary according to their BMD MICs. A solution of 1.25 mg/ml oritavancin in 4% P80/Span 80 (1:1 vol/vol) was used to prepare disks with a final amount of 25 µg oritavancin/disk. Disks were dried overnight at room temperature before use. As shown in Table 16, the inhibition zone diameter for MSSA ATCC 25923 was 22 mm (FIG. 3, left panel), substantially greater than the 15 mm minimum zone diameter recommended by CLSI. Similarly, inhibition zones for MSSA ATCC 29213 and MRSA 33591 were 24 and 22 mm, respectively. Importantly, inhibition zone diameters generally decreased with increasing BMD MIC of the isolate (Table 16). The VISA and hVISA phenotypes also appeared to affect the inhibition zone diameter as no zones were apparent for the VISA isolates NRS402, NRS3 or Mu50 (FIG. 3, middle panel) whereas the hVISA isolate NRS36, with identical BMD MIC to VISA isolates (1 µg/ml), yielded an inhibition zone diameter of 11 mm Furthermore, zone diameters for the tested hVISA isolates NRS2 (FIG. 3, right panel) and NRS36 appeared to have smaller complete inhibition zones relative to wild-type (vancomycin-susceptible, non-hVISA) isolates and had satellite colonies within the zone of inhibition.

TABLE 16

Inhibition zone diameters for S. aureus isolates exhibiting a range of BMD MICs.

| S. aureus isolate | Phenotype | Oritavancin BMD MIC (µg/ml) | Inhibition zone diameter (mm) |
|---|---|---|---|
| ATCC 25923 | MSSA | 0.06 | 22 |
| ATCC 29213 | MSSA | 0.06 | 24 |
| ATCC 33591 | MRSA | 0.06 | 22 |
| U206056 | MRSA | 0.25 | 17 |
| NRS2 | hVISA | 0.25 | 10 |
| NRS36 | hVISA | 1 | 12 |
| Mu50 | VISA | 1 | no zone |
| NRS402 | VISA | 1 | no zone |
| NRS3 | VISA | 1 | no zone |

6) Further validation of the oritavancin disk diffusion assay. The oritavancin disk assay with the newly described conditions (disks impregnated with 20 µl of 1.25 mg/ml oritavancin in 4% P80/Span 80, 1:1 vol/vol); seeding of bacteria with calcium alginate swabs) was further tested against a set of 24 S. aureus isolates in duplicate as follows: 19 clinical isolates with BMD MICs that were representative of the wild-type susceptibility to oritavancin (MIC $MIC_{90}$ of 0.12 µg/ml for S. aureus), two clinical isolates with BMD MICs of 0.25 µg/ml, and the reference isolates MSSA ATCC 25923, hVISA NRS2 and VISA Mu50. As shown in Table 17, the inhibition zone diameters for the 19 wild-type clinical isolates ranged from 20 to 24 mm The two isolates with BMD MICs of 0.25 µg/ml (U206056 and Q670505) both had inhibition zone diameters of 18 mm Inhibition zone diameters for the three reference strains ATCC 25923, hVISA NRS2 and VISA Mu50 were similar to values described previously (compare Table 17 values to those reported in Table 16).

TABLE 17

Inhibition zone diameters obtained for S. aureus clinical isolates and reference strains.

| S. aureus isolate | Phenotype | Oritavancin BMD MIC (µg/ml) | Inhibition zone diameter (mm)[a] |
|---|---|---|---|
| ATCC 25923 | MSSA | 0.06 | 20, 21 |
| NRS2 | hVISA | 0.25 | 12, 12 |
| Mu50 | VISA | 1 | no zones |
| U206056 | MRSA | 0.25 | 18, 18 |
| Q141066 | MSSA | 0.03 | 20, 20 |
| Q670505 | MRSA | 0.25 | 18, 18 |
| S815246 | MSSA | 0.03 | 21, 22 |
| T759545 | MSSA | 0.015 | 22, 22 |
| T998528 | MRSA | 0.015 | 21, 21 |
| U148267 | MSSA | 0.015 | 21, 21 |
| U781969 | MSSA | 0.03 | 22, 23 |
| U933236 | MSSA | 0.06 | 21, 22 |
| V257345 | MRSA | 0.12 | 21, 22 |
| V406957 | MRSA | 0.12 | 21, 21 |
| Q141067 | MRSA | 0.015 | 21, 22 |
| Q670607 | MRSA | 0.03 | 21, 22 |
| S815247 | MSSA | 0.015 | 20, 21 |
| T811355 | MSSA | 0.03 | 21, 22 |
| T998608 | MRSA | 0.03 | 22, 22 |
| U260847 | MRSA | 0.06 | 21, 22 |
| U784439 | MRSA | 0.03 | 20, 20 |
| U933237 | MRSA | 0.12 | 21, 22 |
| V288615 | MRSA | 0.03 | 23, 23 |
| V406985 | MSSA | 0.12 | 24, 24 |

[a]Disks were impregnated with 20 µl of a 1.25 mg/ml oritavancin solution in 4% P80/Span 80 (1:1 [vol/vol]) and allowed to dry overnight at room temperature before use.

The invention of this application has been described above both generically and with regard to specific embodiments. Although the invention has been set forth in what is believed to be the preferred embodiments, a wide variety of alternatives known to those of skill in the art can be selected within the generic disclosure. The invention is not otherwise limited, except for in the recitation of the claims.

All documents, publications, patents, books, manuals, articles, papers, abstracts, posters and other materials referenced herein are expressly incorporated herein by reference in their entireties.

I claim:

1. A disk diffusion assay for determining susceptibility of bacteria to oritavancin, said assay comprising:
   a) impregnating a paper disk with a solution comprising oritavancin, polysorbate 80 and sorbitane monooleate (Span 80),
   b) placing the impregnated disk on the surface of a bacteria-coated media plate,
   c) incubating the plate of b) under conditions promoting bacterial growth, and
   d) measuring a zone of inhibition around the disk.

2. The disk diffusion assay of claim 1, wherein the disk is impregnated with about 25 µg of oritavancin.

3. The disk diffusion assay of claim 2, wherein polysorbate 80 and Span 80 are present in the solution at a ratio of from about 60:40 to about 40:60 v/v and wherein polysorbate 80 and Span 80 are present in the solution at a combined concentration of between about 2.5% and about 5.5% v/v.

4. The disk diffusion assay of claim 2, wherein polysorbate 80 and Span 80 are present in the solution at a ratio of about 50:50 v/v and wherein polysorbate 80 and Span 80 are present in the solution at a combined concentration of about 4% v/v.

5. The disk diffusion assay of claim 2, wherein the impregnated disk is dried at room temperature before it is placed on the bacteria-coated media plate.

6. The disk diffusion assay of claim 2, wherein the incubating step c) is conducted at about 37° C.

7. The disk diffusion assay of claim 2, wherein the zone of inhibition measured in d) is at least about 15 mm in diameter.

8. The disk diffusion assay of claim 1, wherein polysorbate 80 and Span 80 are present in the solution at a ratio of from about 60:40 to about 40:60 v/v and wherein polysorbate 80 and Span 80 are present in the solution at a combined concentration of between about 2.5% and about 5.5% v/v.

9. The disk diffusion assay of claim 1, wherein polysorbate 80 and Span 80 are present in the solution at a ratio of about 50:50 v/v and wherein polysorbate 80 and Span 80 are present in the solution at a combined concentration of about 4% v/v.

10. The disk diffusion assay of claim 1, wherein the impregnated disk is dried at room temperature before it is placed on the bacteria-coated media plate.

11. The disk diffusion assay of claim 1, wherein the incubating step c) is conducted at about 37° C.

12. The disk diffusion assay of claim 1, wherein the zone of inhibition measured in d) is at least about 15 mm in diameter.

13. A disk diffusion assay for determining susceptibility of bacteria to oritavancin, said assay comprising:
   a) impregnating a paper disk with a solution comprising oritavancin, polysorbate 80 and Span 80, wherein the oritavancin is present at a concentration of about 1.25 mg/ml, and wherein the polysorbate 80 and Span 80 are present in the solution at a combined concentration of about 4% v/v and in a ratio of about 50:50 v/v,
   b) placing the impregnated disk on the surface of a bacteria-coated media plate,
   c) incubating the plate of b) under conditions promoting bacterial growth, and
   d) measuring a zone of inhibition around the disk.

14. The disk diffusion assay of claim 13, wherein the disk is impregnated with about 25 µg of oritavancin.

15. The disk diffusion assay of claim 14, wherein the impregnated disk is dried at room temperature before it is placed on the bacteria-coated media plate.

16. The disk diffusion assay of claim 14, wherein the incubating step c) is conducted at about 37° C.

17. The disk diffusion assay of claim 14, wherein the zone of inhibition measured in d) is at least about 15 mm in diameter.

18. The disk diffusion assay of claim 13, wherein the impregnated disk is dried at room temperature before it is placed on the bacteria-coated media plate.

19. The disk diffusion assay of claim 13, wherein the incubating step c) is conducted at about 37° C.

20. The disk diffusion assay of claim 13, wherein the zone of inhibition measured in d) is at least about 15 mm in diameter.

* * * * *